United States Patent [19]
Novick et al.

[11] Patent Number: 5,932,818
[45] Date of Patent: Aug. 3, 1999

[54] NEAR REAL TIME VAPOR DETECTION AND ENHANCEMENT USING AEROSOL ADSORPTION

[75] Inventors: Vincent J. Novick, Downers Grove; Stanley A. Johnson, Countryside, both of Ill.

[73] Assignee: The United States of America as represented by the United States Department of Energy, Washington, D.C.

[21] Appl. No.: 08/941,209

[22] Filed: Sep. 30, 1997

[51] Int. Cl.$^6$ .................................................. G01N 21/01
[52] U.S. Cl. ................... 73/863.22; 73/28.04; 73/28.05; 73/864.81; 250/304; 356/38
[58] Field of Search ........................... 73/863.22, 864.81, 73/28.04, 1.06, 1.05, 28.05; 250/304; 356/38

[56] References Cited

U.S. PATENT DOCUMENTS

| | | | |
|---|---|---|---|
| 3,328,588 | 6/1967 | Steinberg | 73/28.04 X |
| 4,868,398 | 9/1989 | Mulcey et al. | 250/304 X |
| 4,942,297 | 7/1990 | Johnson et al. | 250/304 |
| 5,571,945 | 11/1996 | Koutrakis et al. | 73/28.04 X |

OTHER PUBLICATIONS

Mercer et al. "A Cascade Impactor Operating at Low Volumetric Flow Rates", Atomic Energy Commision–Lovelace Foundation, Fission Product Inhalation Project, Dec. 1962, pp. 1–19.

*Primary Examiner*—Daniel S. Larkin
*Attorney, Agent, or Firm*—Mark F. LaMarre; Mark P. Dvorscak; William R. Moser

[57] ABSTRACT

A vapor sample detection method where the vapor sample contains vapor and ambient air and surrounding natural background particles. The vapor sample detection method includes the steps of generating a supply of aerosol that have a particular effective median particle size, mixing the aerosol with the vapor sample forming aerosol and adsorbed vapor suspended in an air stream, impacting the suspended aerosol and adsorbed vapor upon a reflecting element, alternatively directing infrared light to the impacted aerosol and adsorbed vapor, detecting and analyzing the alternatively directed infrared light in essentially real time using a spectrometer and a microcomputer and identifying the vapor sample.

20 Claims, 13 Drawing Sheets

NEAR REAL TIME VAPOR DETECTION AND ENHANCEMENT USING AEROSOL ADSORPTION

CONTRACTUAL ORIGIN OF THE INVENTION

The United States Government has rights in this invention under Contract No. W-31-109-ENG-38 between the U.S. Department of Energy and the University of Chicago acting through Argonne National Laboratory.

BACKGROUND OF THE INVENTION

This invention relates generally to a method of detecting and analyzing vapor samples, and more particularly, to a method of detecting and analyzing vapor samples in near real time, i.e., on the order of two minutes, using aerosol adsorption.

There is a growing need for detection systems that can aid in verifying compliance with established arms control treaties and/or detect installations that violate such treaties. Ideally, these systems should be mobile so they can be positioned to unambiguously identify a signature source. These systems must be highly sensitive because the measurements must be made from a distance or the source may be shielded or otherwise disguised.

Prior art detection systems have generally fallen into two categories: remote optical sensing and gas sampling. It has been found that these systems have not been as effective as desired in detecting vapor samples having low gas concentrations. Attempts to enhance the detection sensitivity of such prior art detection systems have included using very long single beam paths, multiple beam paths or high powered light sources for the remote optical sensing systems and adsorption/desorption mechanisms or other preconcentration methods for the gas sampling systems. While these methods have increased detection sensitivity, they have otherwise limited the performance capabilities of prior art detection systems.

While very long single beam paths, multiple beam paths or high powered light sources have increased the amount of information in the radiation signal available to the sensors used in remote optical sensing systems, such beam paths and light sources have otherwise limited the mobility of such systems. This is due to space and/or power requirements such systems demand. Such remote optical sensing systems generally must be maintained at remote testing locations or in large mobile units. Alternatively, prior art gas sampling systems that use adsorption/desorption mechanisms or other preconcentration methods to increase detection sensitivity are considered more mobile as compared with the above-discussed remote optical sensing systems. However, while the use of adsorption/desorption mechanisms or other preconcentration methods can increase detection sensitivity, analysis times are also increased.

Thus, there exists a need to improve detection sensitivity of vapor sample detection systems while increasing such detection systems' mobility. There is a further need to provide a detection system to detect and analyze vapor samples in near real time.

Accordingly, a first objective of the present invention is to provide an improved vapor sample detection system with high detection sensitivity.

A further objective is to provide an improved vapor sample detection system that detects and analyzes vapor samples in near real time, i.e. on the order of two minutes.

Yet another objective is to provide an improved vapor sample detection system that is mobile.

Other objectives and advantages of the present invention will become more apparent from the following description and accompanying drawings.

SUMMARY OF THE INVENTION

The above objectives are met or exceeded by the present near real time vapor sample detection method and system. An important feature of the subject invention is the aerosol generated by a nebulizer. Because of its high surface to mass ratio, aerosols collect the vapor sample by adsorbing the vapor onto the surface of the aerosol. The vapor is then concentrated into a compact deposit by impacting the aerosol onto an infrared transparent substrate. Another important feature of the vapor sample detection method and system is the Infrared Aerosol Analyzer ("IAA") which is more fully described in commonly assigned U.S. Pat. No. 4,942,297, incorporated herein by reference. The IAA enhances detection sensitivity by allowing an infrared beam to undergo multiple reflections prior to detection and analysis. These multiple reflections allow multiple interactions between the infrared beam and the vapor bound on the compact aerosol deposit, and is analogous to providing the longer effective path length used in the remote optical sensing systems discussed previously.

More specifically, the present invention includes a vapor sample detection method where the sample contains adsorbed vapor on a collected aerosol. The vapor sample detection method includes the steps of generating a supply of characteristic aerosol that has a particular effective median particle size and specific chemical composition, mixing the aerosol with the vapor sample forming an aerosol with adsorbed vapor suspended in an ambient air stream, impacting the suspended aerosol and adsorbed vapor upon an infrared reflecting element, alternatively directing infrared light to the impacted aerosol and adsorbed vapor sample, detecting and analyzing the alternatively directed infrared light in essentially real time, i.e. on the order of two minutes, and using a spectrometer and a microcomputer to identify the vapor sample.

In another embodiment, the present invention provides an apparatus for analyzing a vapor sample that includes vapor and any ambient air and surrounding natural background particles. This system includes an aerosol generator (nebulizer) that provides a supply of characteristic aerosol with a particular effective median particle size and specific chemical composition. Included in the aerosol generator is an inlet port and an outlet port so that a significant amount of the aerosol is provided at the outlet port. A mixing device provided with an air stream mixes the aerosol with the vapor in a mixing chamber so that the vapor is adsorbed by the aerosol forming an aerosol with adsorbed vapor which is suspended in the air stream. In addition to the mixing chamber, the mixing device has an inlet port in fluid communication with the outlet port of the aerosol generator, a vapor sample inlet port and an exhaust port.

Also included in the present invention is a detecting element. The detecting element has an inlet port in fluid communication with the exhaust port of the mixing device, an exit port, an internal reflecting element (IRE) that removes the aerosol and adsorbed vapor suspended in the air stream via impaction, an infrared light emitter and an infrared light detector. The infrared light is alternatively directed to the aerosol and adsorbed vapor impacted on the IRE and subsequently directed to the infrared light detector for analysis. This analysis is conducted by a spectrometer electrically connected to the infrared light emitter, the infrared light detector, and a microcomputer. In this manner the infrared light can be measured after being alternatively directed to the compact deposit of aerosol and adsorbed vapor on the IRE, and the vapor sample thus identified.

It is preferred that the present vapor sample detection system include a drying and reducing chamber with an inlet aperture connected to the outlet port of the aerosol generator, an outlet aperture connected to the vapor sample inlet port of the mixing element and a drying chamber. The drying chamber provides sufficient time for water associated with the aerosol to evaporate while, at the same time, reduces the aerosol's effective median particle size to the desired size for impaction on the IRE. Further, the present system can include a High Efficiency Particulate Air (HEPA) filter connected to the vapor sample inlet port of the mixing device so that the sample vapor is separated from surrounding natural background particles in the ambient air. Additionally, the preferred embodiment includes a virtual impactor that separates the aerosol into a plurality of fractions having different size particles and a pair of opposing slit nozzles which direct one fraction of the plurality of fractions against opposing sides of the internal reflecting element. Moreover, this present vapor sample detection system is essentially self-contained and portable for use in mobile units and field sites.

DESCRIPTION OF THE PREFERRED EMBODIMENT

Figure 1:
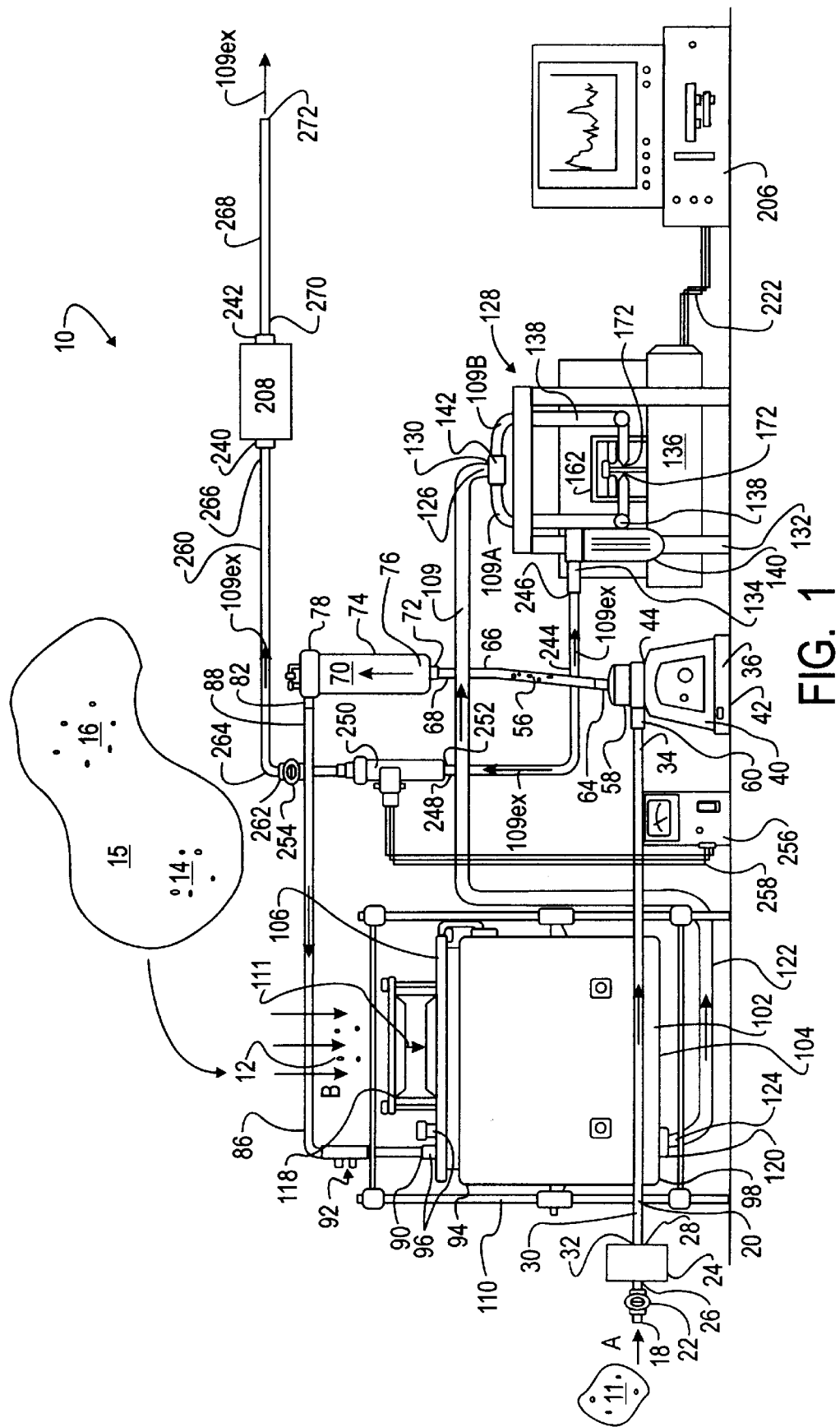
FIG. 1 is a schematic representation of the near real time vapor sample detection system in accordance with the present invention.

Referring to FIG. 1, a vapor sample detection system, generally designated 10 having a source of clean air 11, is supplied with a vapor sample 12 which is to be analyzed. The source of clean air 11 could be provided by a compressed air source (not shown) or an exhaust conduit which is discussed in detail below. The vapor sample 12 includes a vapor 14, and any ambient air 15 and surrounding natural background particles 16 contained therein. In the embodiment depicted in FIG. 1, the vapor sample detection system 10 includes an air inlet 18 through which the clean air 11 is supplied to the vapor sample detection system 10 by an air flow 20 in the general direction indicated by arrow A. In the depicted embodiment, a first flow valve 22 is joined to, and in fluid communication with, the air inlet 18 and a first flow meter 24 having a meter inlet 26 and a meter outlet 28, where the first flow valve 22 is connected to, and in fluid communication with, the meter inlet 26. Further shown in the depicted embodiment, an air flow delivery conduit 30, having a conduit inlet 32 and a conduit outlet 34 opposite the conduit inlet 32, is in communication with both the meter outlet 28 of the first flow meter 24 and an aerosol generator 36. Specifically the conduit inlet 32 is joined to, and in fluid communication with, the meter outlet 28 of the first flow meter 24 and the conduit outlet 34 is joined to, and in fluid communication with, the aerosol generator 36. Preferably, the air flow delivery conduit 30 is a tube with a tube inlet and a tube outlet opposite the tube inlet. In this manner, the air flow 20 is directed from the first flow meter 24 through the air flow delivery conduit 30 into the aerosol generator 36 in the direction indicated generally by arrow A at a preferred rate of 5 liters per minute (LPM).

Figure 2:
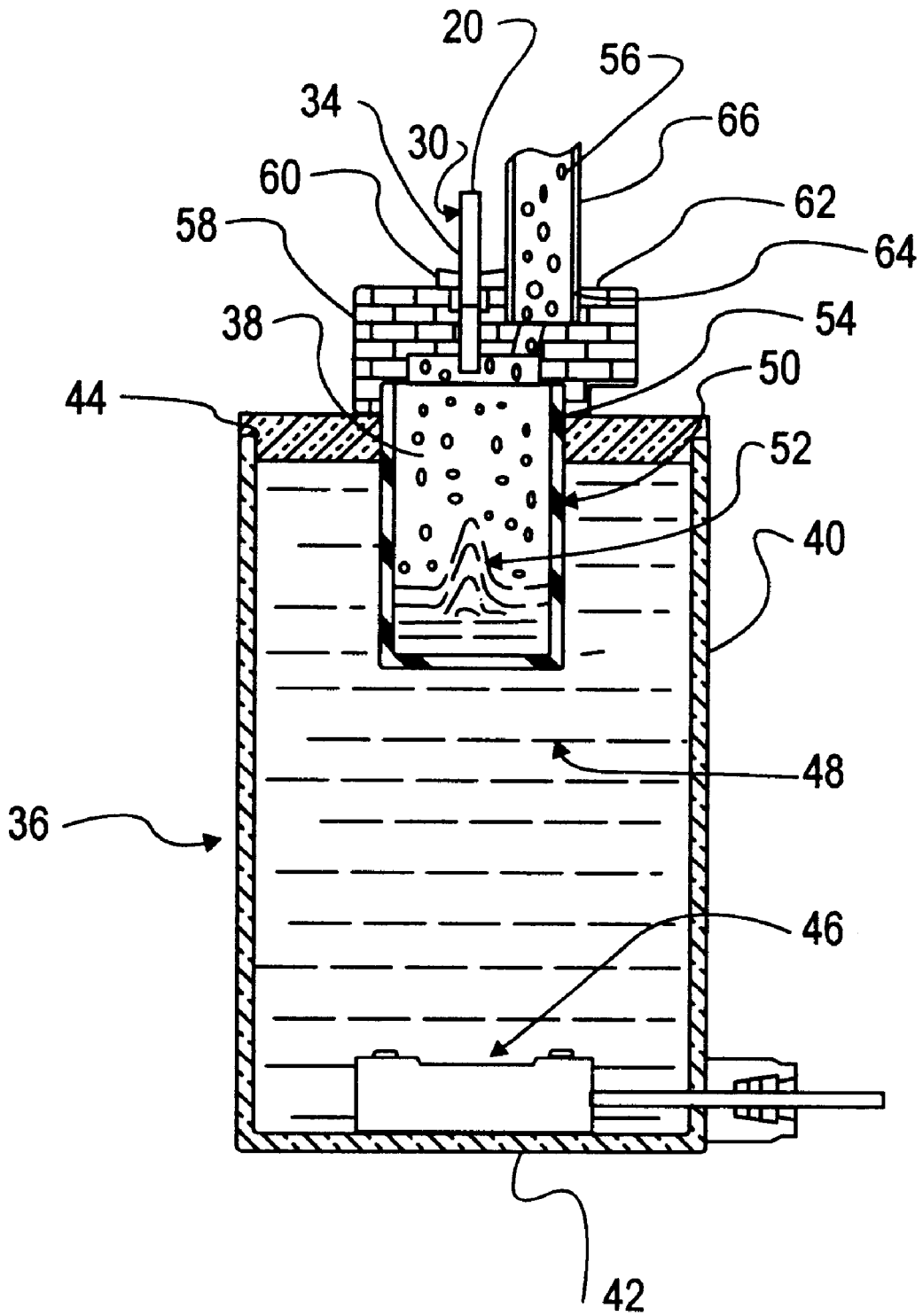
FIG. 2 is side cross-sectional view of a representative ultrasonic nebulizer shown in FIG. 1.

Referring now to FIG. 2, an aerosol 38 is generated by the aerosol generator 36. In one embodiment depicted in FIG. 2, the aerosol generator 36 is a commercially available generator having a generally cylindrical shape formed by a generator housing 40 with a closed end 42, a discharge end 44, a powered transducer assembly 46 attached to the closed end 42, and a coupling fluid 48 contained in the generator housing 40 and in contact with the powered transducer assembly 46. A cup-like generator reservoir 50 containing an aerosol material 52 is inserted through an opening 54 in the discharge end 44 and is in contact with the coupling fluid 48. Upon engaging the powered transducer assembly 46, mechanical energy is transmitted to the coupling fluid 48 in a known manner, causing the coupling fluid 48 to vibrate. These vibrations are in turn transmitted to the generator reservoir 50, which generates the aerosol 38 so that the aerosol 38 become suspended in the air flow 20 forming a suspended aerosol 56.

It is significant to note that the aerosol 38 selected to form the suspended aerosol 56 must adsorb and/or chemically react with the vapor 14. While both a solid (dry powder) or an aqueous solution that dries to a solid powder can be used, it has been found that aqueous solutions are preferable in that they afford greater control of particle size with a stable output concentration. Further, while a number of known gas trapping materials, such as molecular sieves and gas chromatography adsorbents were tested, they were found to be unsuitable for this application. It has been found that aerosols generated from dissolved chemicals in an aqueous solution, preferably cupric chloride, cupric sulfate, and magnesium oxide, were effective at capturing the vapor 14. Preferably the aerosol 38 is formed from a solution that results in a suspended aerosol 56 with a mass median aerodynamic diameter between about 0.3 to about 2.5 micrometers.

Both FIGS. 1 and 2 depict a generator cap member 58, having an inlet port 60 and an outlet port 62, joined to the discharge end 44 so that the generator cap member 58 covers the generator reservoir 50. The inlet port 60 is joined to and in fluid communication with the conduit outlet 34 of the air flow delivery conduit 30, while the outlet port 62 is further joined to, and in fluid communication with, an aerosol conduit inlet 64 of an aerosol delivery conduit 66 which has an aerosol conduit outlet 68 opposite the aerosol conduit inlet 64. Preferably, the aerosol delivery conduit 66 is a tube, with a tube inlet and a tube outlet opposite the tube inlet. As provided above, the air flow 20 is transmitted to the generator reservoir 50 of the aerosol generator 36 by means of the air flow delivery conduit 30. The aerosol 38, formed in the generator reservoir 50 as described above, is entrained by the air flow 20 so that a significant amount of the aerosol 38 is suspended in the air flow 20 forming the suspended aerosol 56 at the outlet port 62. While the rate of the air flow 20 may vary depending on the sampling required, preferable the air flow 20 is nominally set at a rate of 5 LPM. Although the aerosol generator 36 described above is preferred, any aerosol generation method can be used. An aerosol generator 36 is contemplated that uses a source of compressed air or other means to provide the suspended aerosol 56 at the outlet port 62 such that the air flow delivery tube 30 connected to the aerosol generator 36 is not required.

Figure 3:
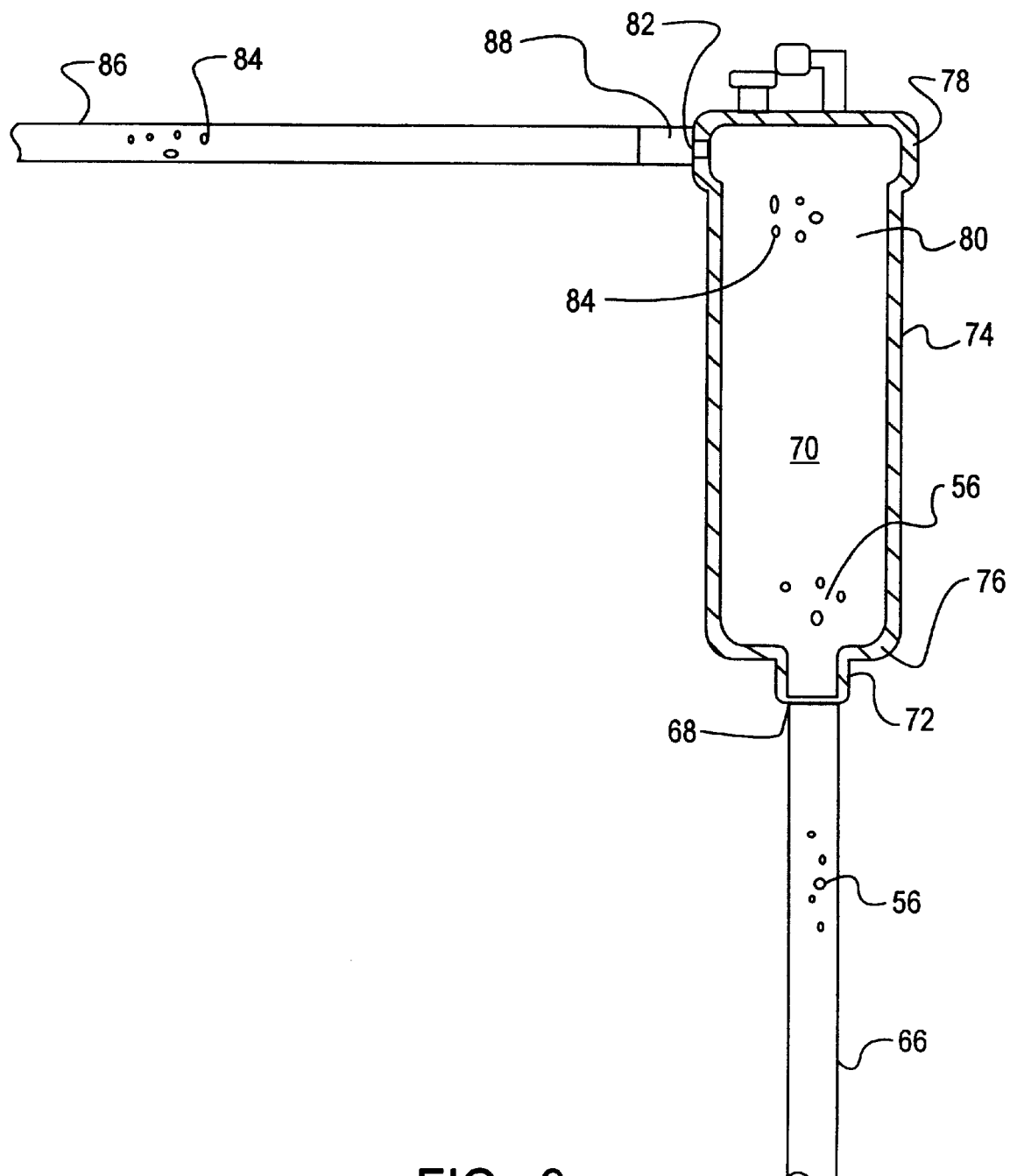
FIG. 3 is side cross-sectional view of the drying chamber shown in FIG. 1.

Another feature of the vapor sample detection system 10 is a drying receptacle 70, having an inlet aperture 72 joined to, and in fluid communication with, the aerosol conduit outlet 68 of the aerosol delivery conduit 66 as depicted in FIG. 3. Upon further inspection of FIG. 3 it is evident that the drying receptacle 70 has a generally cylindrical shape with a receptacle housing 74, an inlet end 76 and an outlet end 78 forming a drying chamber 80. An outlet aperture 82 is further formed in the outlet end 78 of drying receptacle 70 so that the outlet aperture 82 is in fluid communication with the drying chamber 80. Preferably, the drying chamber 80 is large enough so that any water associated with the suspended aerosol 56 has sufficient time to evaporate, forming a dried, suspended aerosol 84. It should be noted that drying the suspended aerosol 56 reduces its effective median particle size, enabling the dried, suspended aerosol 84 to be transported through the vapor sample detection system 10 with minimal wall loss. After drying, the dried, suspended aerosol 84 has an effective median particle size of about 0.3 micrometers to about 2.5 micrometers.

Again referring to FIG. 1, a dried aerosol delivery conduit 86 is depicted, where the dried aerosol delivery conduit 86 has a dried aerosol conduit inlet 88, joined to, and in fluid communication with, the outlet aperture 82 of the drying receptacle 70 and a dried aerosol conduit outlet 90 opposite the dried aerosol conduit inlet 88. Preferably, the dried aerosol delivery conduit 86 is a tube with a tube inlet and a tube outlet opposite the tube inlet. In one embodiment, the dried aerosol delivery conduit 86 has an injection port 92 with a plurality of injection openings, so that additional material may be added to the vapor sample detection system 10, if desired. In order to test the vapor sample detection system 10, the injection port 92 was utilized to introduce vapor 14 therein, however in the preferred embodiment the injection port 92 is not used (except for calibration) or may even be eliminated entirely. As shown, a mixing receptacle 94 having at least one aerosol inlet port 96, is joined to, and in fluid communication with, the dried aerosol conduit outlet 90. The dried aerosol delivery conduit 86 provides a method by which the dried, suspended aerosol 84 is transmitted from the drying chamber 80 to the mixing receptacle 94.

Figure 4:
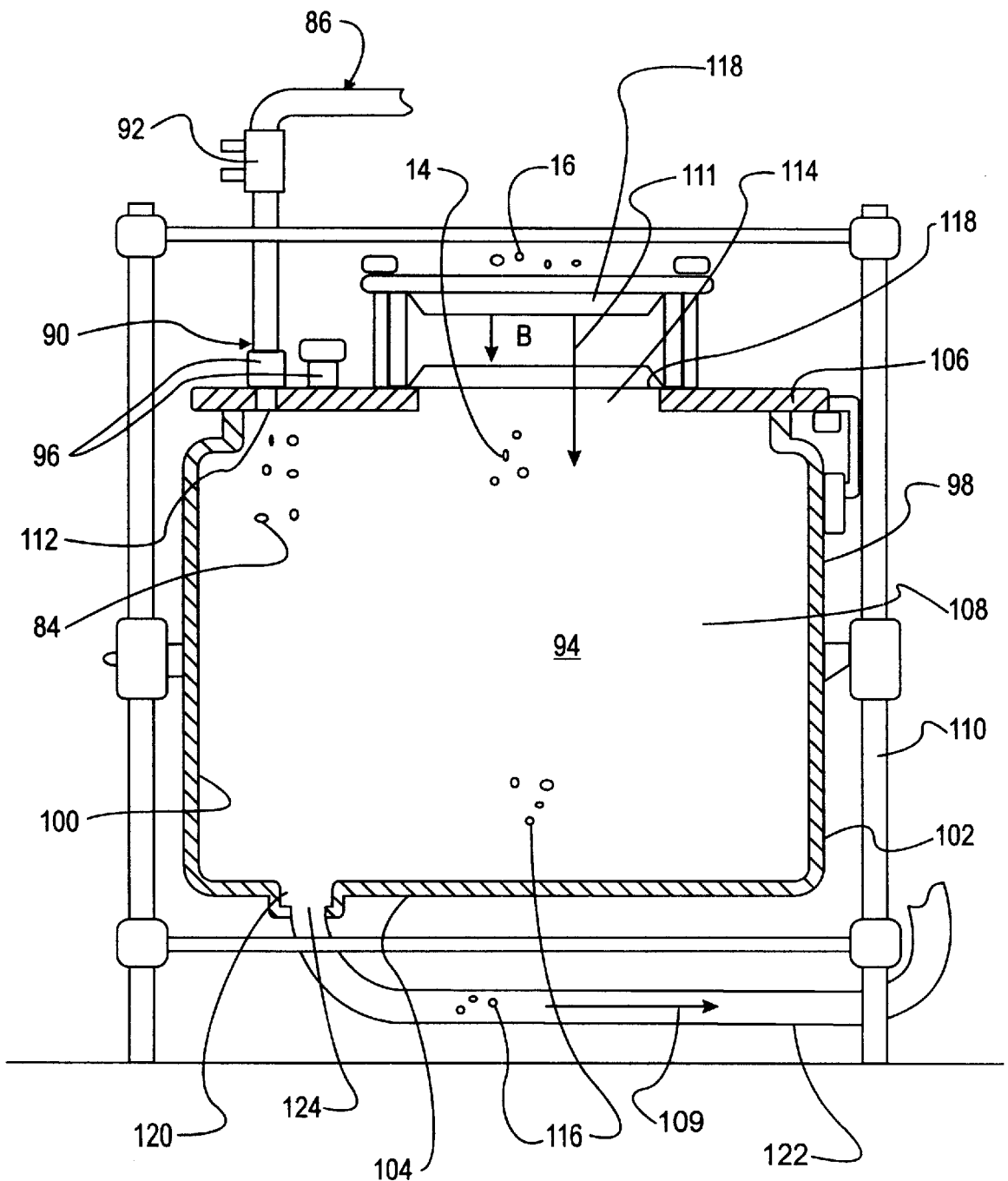
FIG. 4 is a side cross-sectional view of the mixing chamber shown in FIG. 1.
Figure 5:
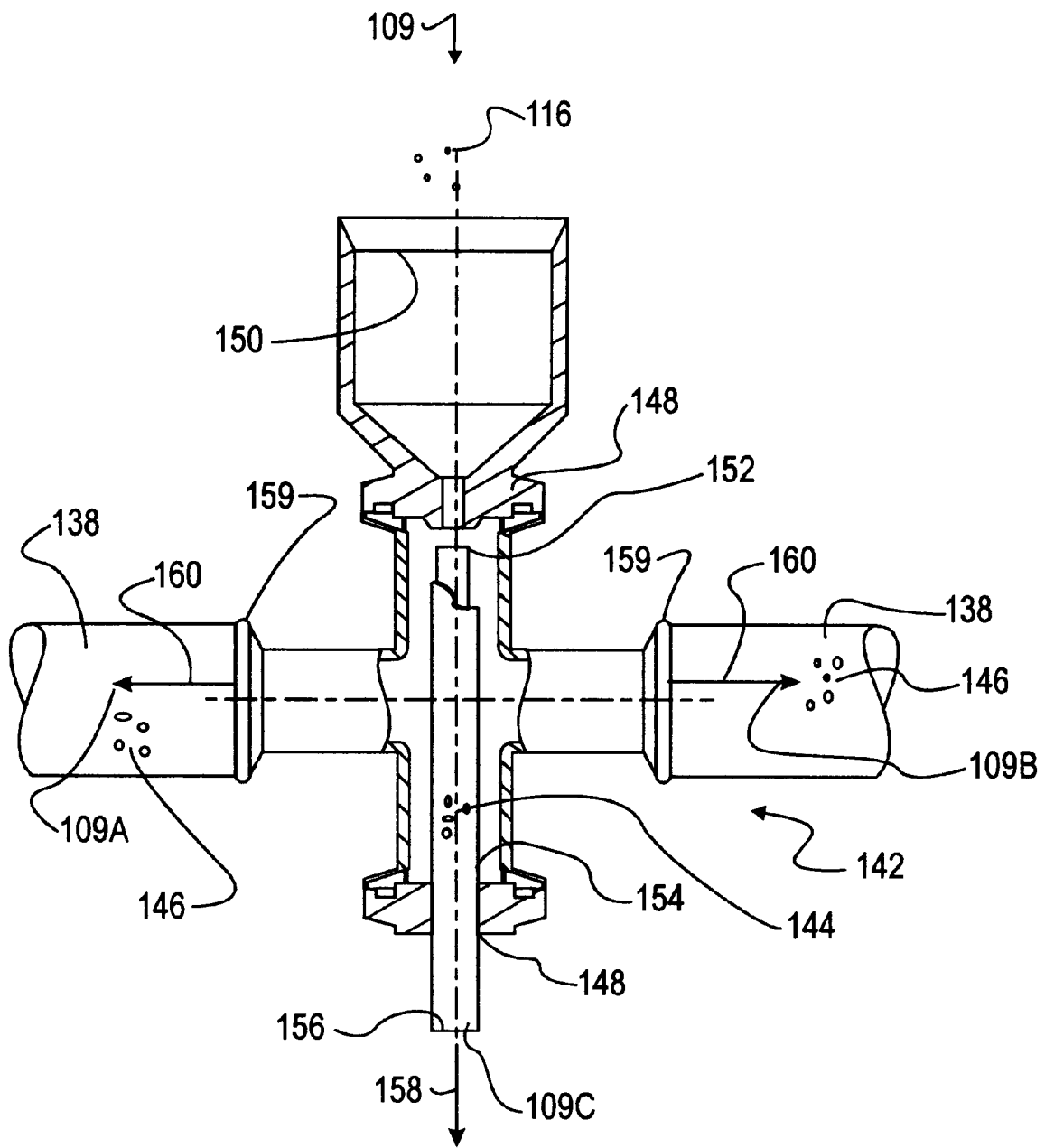
FIG. 5 is a side cross-sectional view of the virtual impactor shown in FIG. 1.

One embodiment of the mixing receptacle 94 depicted in FIG. 4 is formed by a mixing housing 98 with an inner surface 100 and an outer surface 102, a discharge end 104 and an inlet end 106, where the inner surface 100 and the discharge and inlet ends 104 and 106 respectively form a mixing chamber 108. As shown, the mixing receptacle 94 has a support structure 110 attached to the outer surface 102, however the support structure 110 may not be required depending upon the mixing receptacle 94 selected. Further, the mixing chamber 108 must be large enough so that the dried, suspended aerosol 84 has sufficient time to interact with the vapor 14. Preferably, the mixing chamber 108 should allow a minimum residence time of 2 seconds. Specifically, this requires that the mixing chamber 108 have a volume of at least 2.5 liters.

As described above, the embodiment depicted in FIG. 4 details at least one aerosol inlet port 96 joined to, and in fluid communication with, the inlet end 106 of the mixing receptacle 94 at an aerosol inlet 112. In addition to the at least one aerosol inlet port 96, the inlet end 106 also includes at least one vapor sample inlet port 114 in fluid communication with the vapor sample 12 and the mixing chamber 108. In this manner, the vapor sample 12, including the vapor 14, and the ambient air 15 and surrounding natural background particles 16, is drawn into the mixing chamber 108 by a vacuum pump 208 (not shown) creating an air stream 111 in the general direction indicated by arrow B. While the rate of the air stream 111 may vary depending on the sampling required, preferable the air stream 111 is nominally set at a rate of 55 LPM.

The vapor 14 interacts with, and is adsorbed by, the dried, suspended aerosol 84 forming an aerosol and adsorbed vapor 116 suspended in the air stream 111. Preferably, the mixing receptacle 94 separates the surrounding natural background particles 16 from the vapor sample 12, so that only the vapor 14 interacts with, and is adsorbed by, the dried, suspended aerosol 84 forming the aerosol and adsorbed vapor 116. Such separation can be performed by a number of methods, but in the depicted embodiment is accomplished using at least one filter 118 joined to outer surface 102 and in fluid communication with the vapor sample inlet port 114. Specifically, this separation is accomplished by employing at least one HEPA filter 118. In this manner, the surrounding natural background particles 16 are separated from the ambient air 15 and the vapor 14 in the vapor sample 12, thus preventing potential interference in the spectral analysis. When used in the field, it is contemplated that the filter 118 may be not be required and thus eliminated.

Further included in the mixing receptacle 94 is an exhaust port 120 formed in the discharge end 104 of the mixing receptacle 94. The exhaust port 120 is joined to and in fluid communication with an aerosol and vapor delivery conduit 122 at an inlet end 124 thereof. Referring back to FIG. 1, the aerosol and vapor delivery conduit 122 has an outlet end 126 opposite the inlet end 124 which in turn is connected to a detector 128 at an inlet port 130. Preferably, the aerosol and vapor delivery conduit 122 is a tube, with a tube inlet and a tube outlet opposite the tube inlet. This arrangement allows the aerosol and adsorbed vapor 116 to be exhausted from the mixing receptacle 94 to the detector 128 by an airstream 109 using the aerosol and vapor delivery conduit 122 after the dried, suspended aerosol 84 and the vapor 14 have had sufficient time to interact in the mixing chamber 108. While the rate of the air stream 109 may vary depending on the sampling required, preferable the air stream 109 is nominally set at a rate of 60 LPM, where preferably the rate of the air stream 109 equals the rate of the air flow 20 plus the rate of the air stream 111.

Referring again to FIG. 1, the detector 128 is depicted with a detector support frame 132, an outlet port 134, and an analyzer 136. The detector 128 includes two opposing supply conduits 138 joined to, and in fluid communication with, the inlet port 130. Preferably, the outlet port 134 includes an exhaust filter 140 to trap any particles contained in the air stream 109 exhausted there from (the air stream 109 exhausted from the outlet port 134 and the exhaust filter 140 is referred to as air stream 109ex for clarity). It is contemplated that, the outlet port 272 could be in fluid communication with the air inlet 18 so that a portion of the exhaust air stream; 109ex acts as the source of clean air 11.

Figure 6:
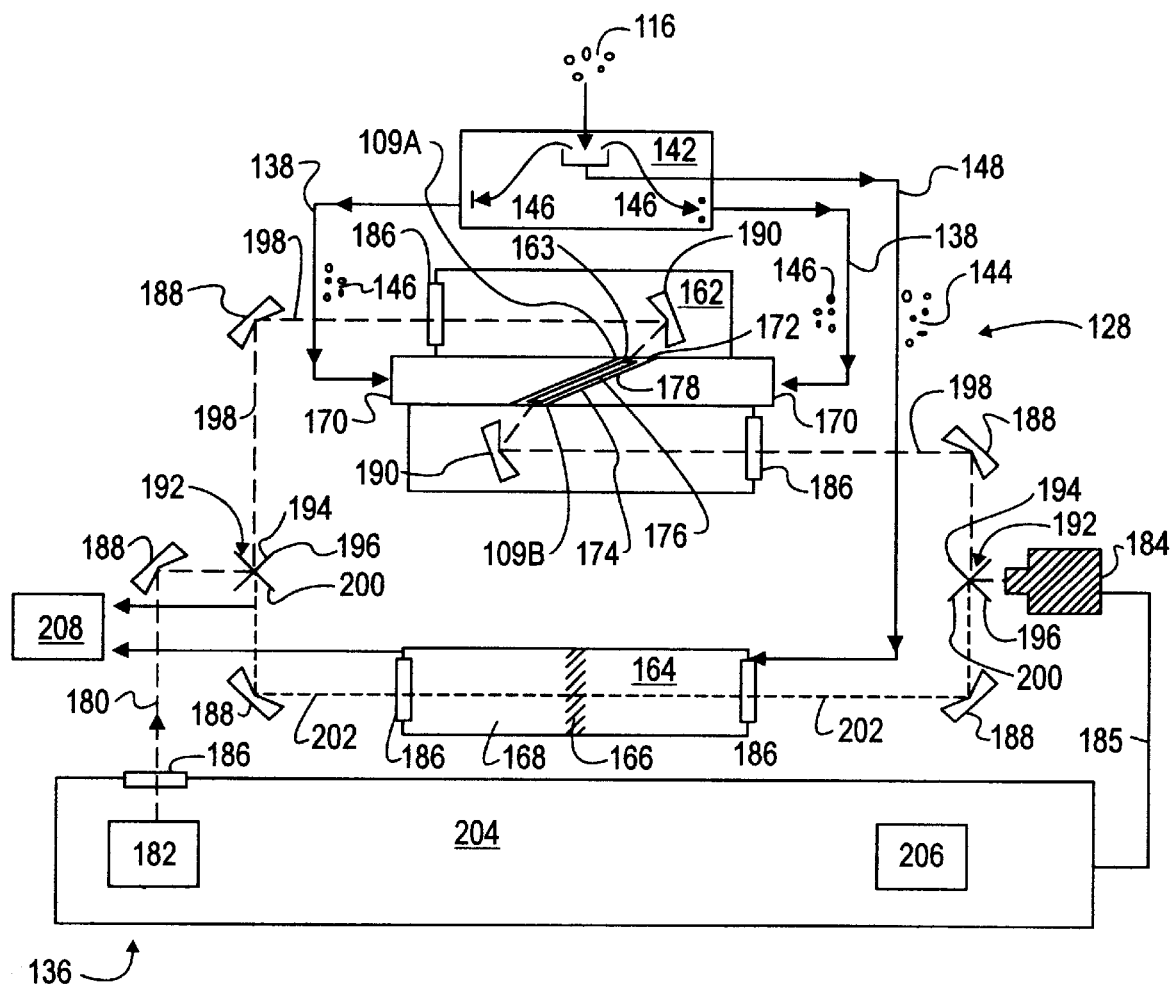
FIG. 6 is a schematic representation of the infrared aerosol analyzer ("IAA") shown in FIG. 1.

Specifically, the analyzer 136 is an Infrared Aerosol Analyzer (IAA) shown in FIG. 6. The analyzer 136 is configured to separate the aerosol and adsorbed vapor 116 into a plurality of fractions having different size particles. Preferably, the analyzer is configured to analyze particles having an aerodynamic diameter between about 0.3 micrometers to about 2.5 micrometers. Separation is accomplished using a virtual impactor 142 that separates the aerosol and adsorbed vapor 116 into at least two fractions which includes coarse particles 144 and fine particles 146, where the fine particles 146 make up the majority of the total aerosol and adsorbed vapor 116. For this purpose, particles are considered ultra-fine if they are less than about 0.3 micrometers in aerodynamic diameter, fine if they are between about 0.3–2.5 micrometers in aerodynamic diameter, and coarse if they are greater than about 2.5 micrometers in aerodynamic diameter.

The inlet port 130 is in fluid communication with the virtual impactor 142. Turning now to FIG. 5, the virtual impactor 142 is shown in greater detail with an impactor housing 148. The aerosol and adsorbed vapor 116 suspended in the air stream 109 enters the virtual impactor 142 through an impactor inlet 150 formed by the impactor housing 148 and which is joined to, and in fluid communication with, the outlet end 126 of the aerosol and vapor delivery conduit 122. The virtual impactor 142 includes a knife-edge opening inlet 152 formed in a coarse supply conduit 154 connected to, and in fluid communication with, a coarse particle outlet 156 formed by the impactor housing 148. The knife-edge opening inlet 152 is configured so that the aerosol and adsorbed vapor 116 is divided into a plurality of fractions and the air stream 109 is divided into a plurality of air streams, a first, second and third air streams 109A, 109B and 109C respectively. In the preferred embodiment, one fraction, making up the majority of the aerosol and adsorbed vapor 116 including all the fine particles 146 (and any ultra-fine particles), is carried around the knife-edge opening inlet 152 by the first and second air streams 109A and 109B. Another fraction, containing the coarse particles 144, follows a relatively straight path along the coarse particle path 158 carried by the third air stream 109C, exiting the virtual impactor 142 via the coarse supply conduit 154. The fine particles 146 are drawn through a pair of opposing supply conduit openings 159 along paths 160 so that one portion of the fine particles 146 is carried along by the first air stream 109A down one of the pair of opposing supply conduits 138 and the remaining portion of the fine particles 146 is carried along by the second air stream 109B down the remaining opposing supply conduit 138, where the two portions of the fine particles 146 are substantially equal. The pair of opposing supply conduit openings 159, which are formed by the impactor housing 148, are in turn joined to, and in fluid communication with, the opposing supply conduits 138, so that the fine particles 146 are drawn down the pair of opposing supply conduits 138 past the pair of opposing supply conduit openings 159 in to an attenuated total internal reflection ("ATR") impactor 162 (not shown). In such manner, the coarse particles 144 are separated from the fine particles 146.

The fraction of the vapor 14 that includes the coarse particles 144 is routed through the coarse particle path 158 to a coarse particle collector 164, which includes an internal filter 166 and a coarse filter chamber 168, shown in FIG. 6. If analysis of the coarse particles 144 is desired, a PTFE or similar filter (not shown) which allows passage of infrared light could be used for the internal filter 166. Alternatively, the coarse particle path 158 could be replaced with a HEPA filter (not shown) to collect and discard the coarse particles 144. The fraction of the vapor 14 which includes the fine particles 146 is split and routed as shown at 147 through the two opposing supply conduits 138 to a pair of opposing slit nozzles 170 in an impact chamber 172 contained in the ATR impactor 162. Further contained in the ATR impactor 162 is at least one internal reflecting element ("IRE") 174. Note that the present invention is not limited to a specific number or configuration of the IRE's 174. It is important to note that the virtual impactor 142 is essential when the vapor sample detection system 10 is used as a field instrument sampling unfiltered air. In such case, the virtual impactor 142 would prevent coarse particles 144, i.e. greater than 2.5 micrometers, from impacting on the IRE 174.

The IAA discussed above is shown in FIG. 6 in detail. As shown, the fine particles 146 are provided with sufficient velocity by the pair of opposing slit nozzles 170 to impact and adhere to opposing sides of an outer surface 176 of the at least one IRE 174, forming an impacted aerosol and adsorbed vapor 178 (shown in detail in FIG. 8). The above described arrangement provides for the fraction that includes the coarse particles 144 to be routed along the coarse particle path 158 to the coarse particle collector 164 where, after passing through the internal filter 166, the coarse particles 144 are collected in the coarse filter chamber 168, while any ultra-fine particles (not shown) would follow the first and second air streams 109A and B around the at least one IRE 174 and be discarded. In this manner, only the fine particles 146 impact and adhere to the outer surface 176 of the at least one IRE 174, forming the impacted aerosol and adsorbed vapor 178 on the outer surface 176.

It should be noted that if capture and analysis of ultra-fine particles (not shown) is desired, the coarse particle collector 164, using a similar internal filter, could be used as long as the filter is capable of capturing ultra-fine particles. Further, the size ranges or "cut points" of the plurality of fractions can be determined by selecting appropriate nozzles and/or the gas flow rate for the pair of opposing slit nozzles 170.

FIG. 6 further depicts an infrared light 180 generated by an infrared light emitter 182 that is eventually directed to an infrared light detector 184. The coarse particle collector 164 and the ATR impactor 162 contain a plurality of windows 186 that pass the infrared light 180 without significant reflection or attenuation. The present invention is not limited to the number, configuration or material of the windows 186. Preferably, the windows 186 are made of potassium bromide (Kbr), however, any other suitable infrared transmitting material is contemplated. Additionally, a plurality of mirrors 188 are provided, as needed, to focus and route the infrared light 180 through the coarse particle collector 164, in addition to the ATR impactor 162, to the infrared light detector 184. A plurality of parabolic mirrors 190 are provided in the impact chamber 172 to focus and direct the infrared light 180 to the impacted aerosol and adsorbed vapor 178 and the at least one IRE 174, as discussed in greater detail below.

Additionally, the present invention includes a plurality of moveable mirrors 192 having a reflecting surface 194 which direct the infrared light 180 alternatively through the coarse particle collector 164 and the impact chamber 172. When the moveable mirrors 192 are orientated in a first position 196 shown in FIG. 6, the infrared light 180 passes through the impact chamber 172 along a first light path 198. When the moveable mirrors 192 are moved to a second position 200, the infrared light 180 is directed through the coarse particle collector 164 along a second light path 202.

An important feature of the present invention is the analyzer 136, depicted in FIG. 6 electrically connected with cable 185 to both the infrared light emitter 182 and the infrared light detector 184. Preferably, the analyzer 136 includes a commercially available fourier-transform spectrometer 204, and may contain the infrared light emitter 182 in addition to a dedicated microcomputer 206, which may include a monitor and plotter (not shown). The spectrometer 204 could be a Bomen Michelson 100 spectrometer or other suitable device, which can measure and analyze the infrared spectrum from 400 to 4000 wavenumber ($cm^{-1}$) every nine seconds.

In operation, the IRE 174 is impacted by the fine particles 146 contained in the aerosol and adsorbed vapor 116 suspended in the first and second air streams 109A and 109B, generated by the vacuum pump 208 shown in both FIGS. 1 and 6, forming the impacted aerosol and adsorbed vapor 178. The infrared light 180 generated by the infrared light emitter 182 passes through window 183; and is then alternatively directed to the impacted aerosol and adsorbed vapor 178 and the IRE 174, using the plurality of moveable mirrors 192 orientated in the first position 196, in conjunction with the plurality of mirrors and parabolic mirrors 188 and 190 respectively, so that the infrared light 180 is directed along a first light path 198. The alternatively directed infrared light 180 is then detected by the infrared light detector 184, which in turn is electrically connected with cable 185 to the analyzer 136, containing the spectrometer 204 and the microcomputer 206, so that infrared light 180 can be measured and analyzed, and the vapor sample 12 determined.

Figure 7:
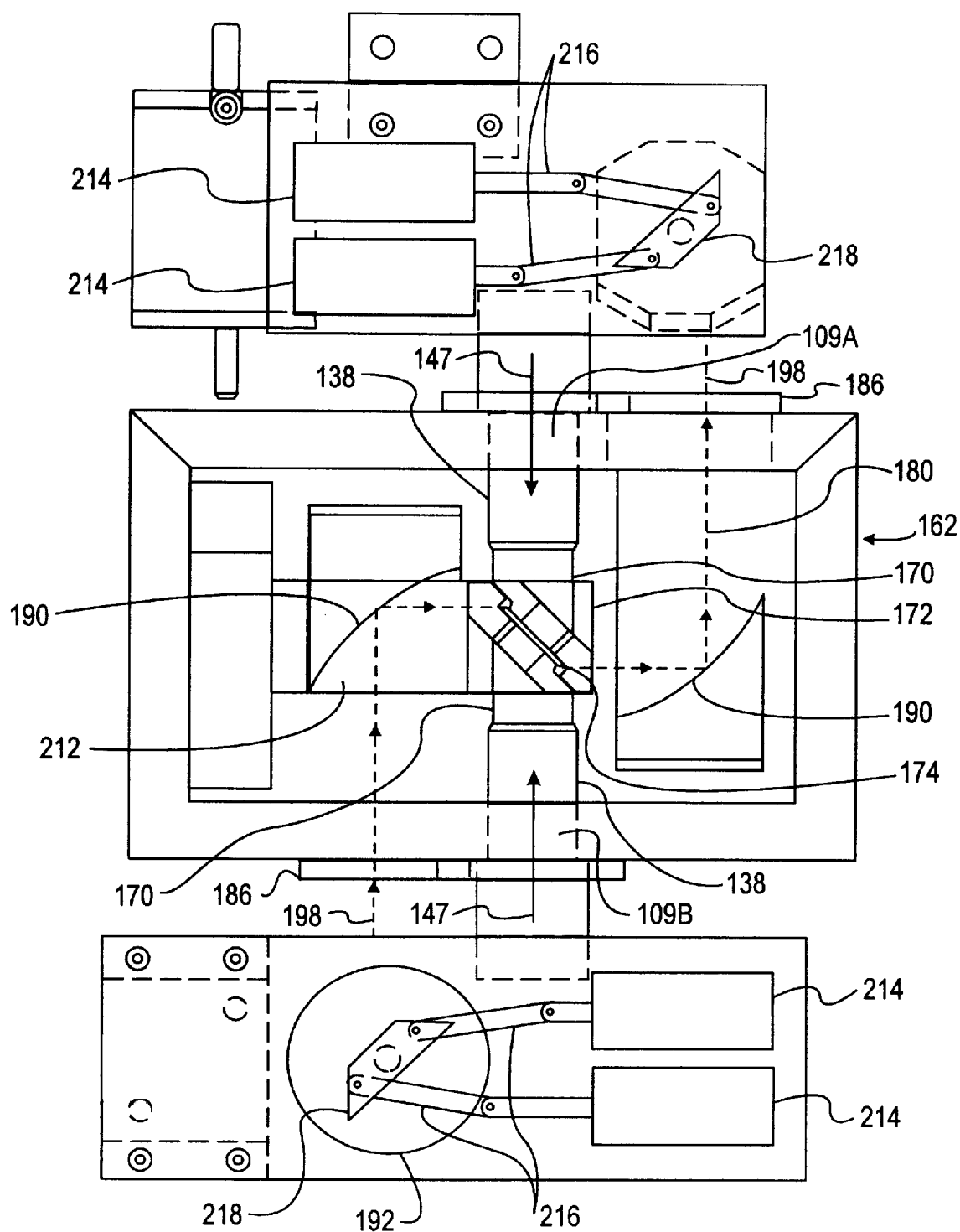
FIG. 7 is a top view of the attenuated total internal reflection ("ATR") impactor and mirror movement mechanism shown in FIG. 6.
Figure 8:
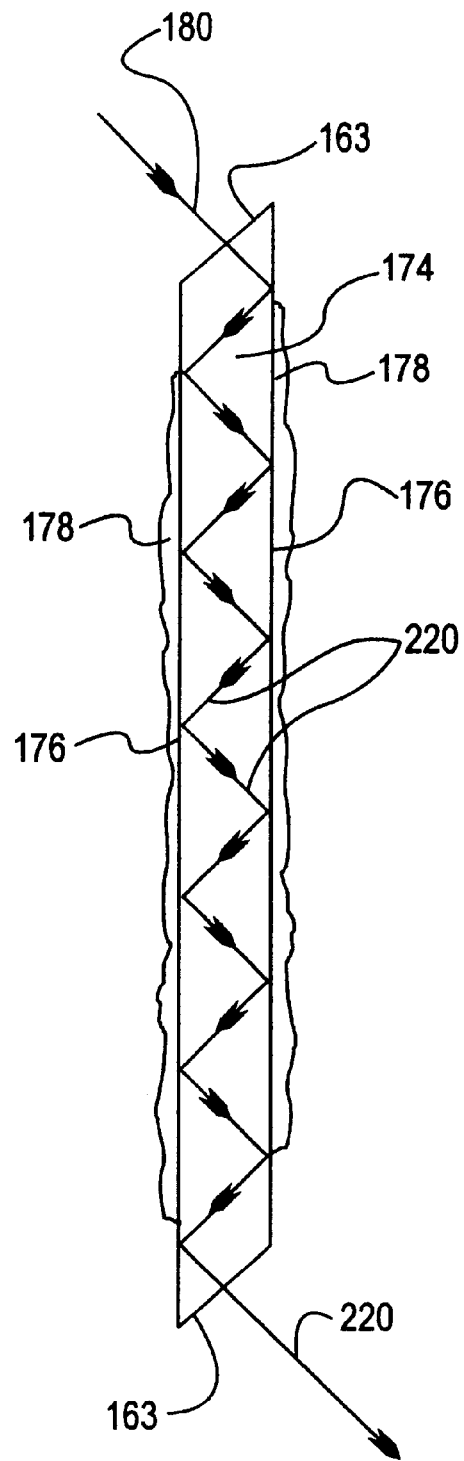
FIG. 8 is a side cross-sectional view of the internal reflecting element ("IRE") shown in FIG. 6, with a sample material deposited thereon.
Figure 9:
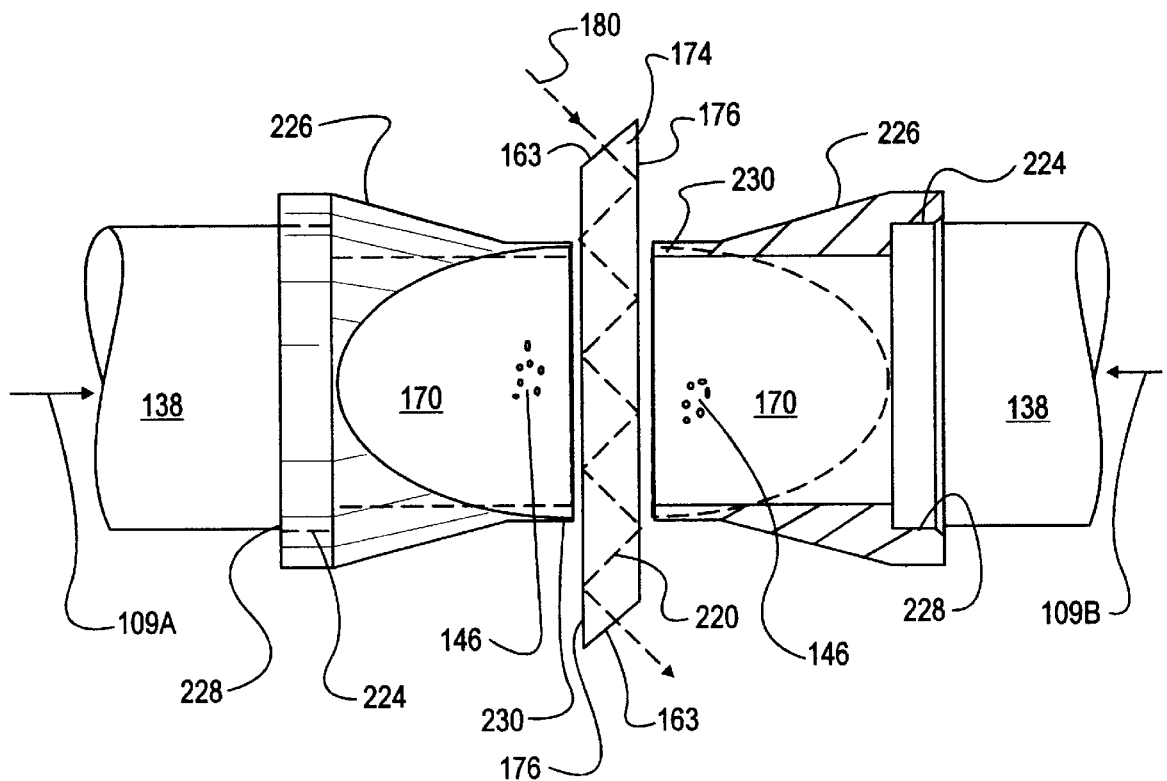
FIG. 9 is side view of the opposing slit-nozzles shown in FIG. 6, with one of the slit nozzles and the IRE shown in cross-section.
Figure 10:
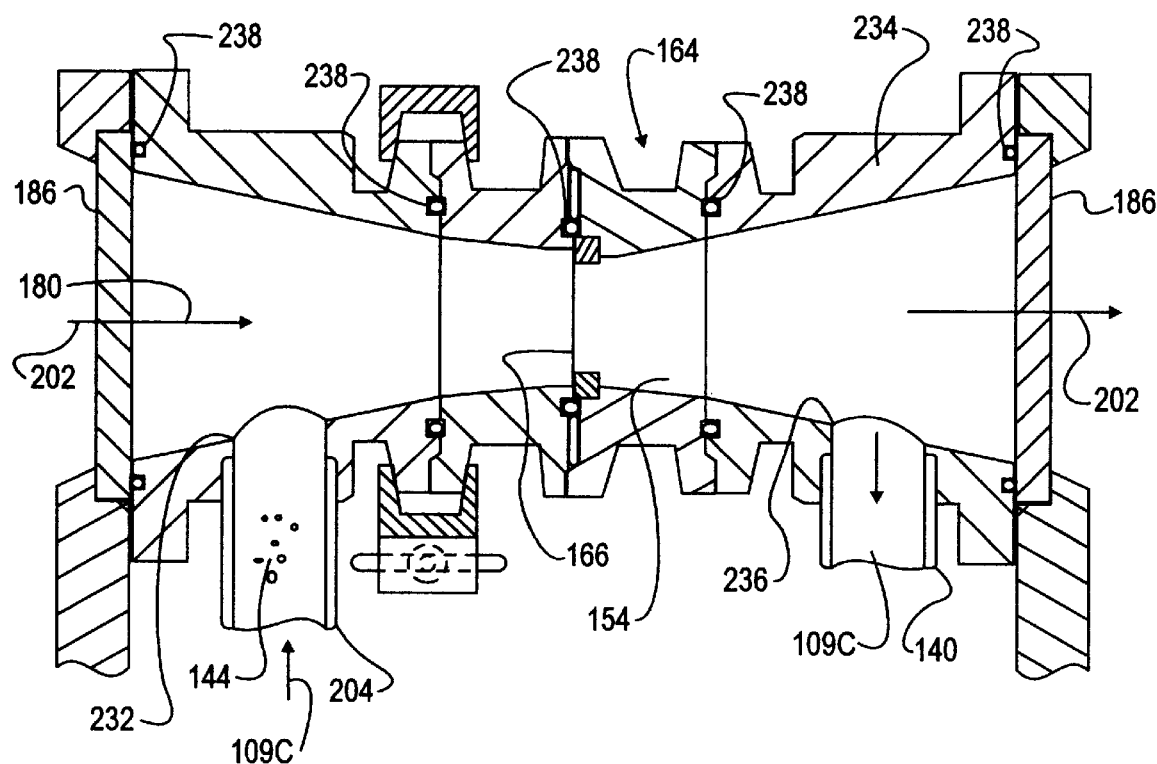
FIG. 10 is a side cross-sectional view of the coarse particle collector shown in FIG. 6.

FIG. 7 depicts the ATR impactor 162 in greater detail. Included in the ATR impactor 162 is the impact chamber 172 containing the pair of opposing slit nozzles 170 and at least one of a plurality IRE 174 which act as a collection substrate for the fine particles 146. It should be noted that an ATR impactor 162 containing up to 20 IREs 174 is contemplated. Multiple IRE's 174 can move across the pair of opposing slit nozzles 170 in the plane perpendicular to the view shown in FIG. 7 at any desired rate of speed. Such multiple IRE's 174 can be shifted in and out of a collection zone 212 or remain stationary, if desired. The drive mechanism (not shown) for the multiple IRE's 174 can be computer controlled so that the IRE's 174 can be either automatically or manually sequenced in and out of the collection zone 212 between the pair of opposing slit nozzles 170.

The ATR impactor 162 is preferred for collecting the fine particles 146 fraction because the fine particles 146 can be efficiently collected by impaction. Specifically, the penetration depth of infrared light 180 is of the same order of magnitude as the diameter of the fine particles 146. In the preferred embodiment, the penetration depth of the evanescent wave of the infrared light 180 ranges from about 1.5 micrometers to about 3 micrometers.

Movement of the moveable mirrors 192 depicted in FIG. 6 is controlled by a plurality of solenoids 214, as shown in FIG. 7. The solenoids 214 move a plurality of arms 216 which turn plates 218. The plates 218 are secured to the moveable mirrors to direct the moveable mirrors 192 as desired. As described above, when the moveable mirrors 192 are moved to the first position 196 (not shown in FIG. 7) by the solenoids 214, the arms 216 and the plates 218, the infrared light 180 is directed to the impacted aerosol and adsorbed vapor 178 and the IRE 174 along the first light path 198.

An important feature of the present invention, the IRE 174, is shown in greater detail in FIG. 8. Preferably, the IRE 174 has a trapezoidal shape with the dimensions of 25 mm×5 mm×2 mm. Specifically, the IRE 174 is made of zinc selenide (ZnSE), however, other materials such as KRS-5, a material made of thallium bromide/thallium iodide, are contemplated, as long as the material is transparent to the infrared light 180, inert, and resists scratching. The fine particles 146 are impacted on the opposing outer surfaces 176 by the pair of opposing slit nozzles 170 (not shown) forming the impacted aerosol and adsorbed vapor 178. The infrared light 180 is focused by the mirrors, parabolic mirrors and moveable mirrors 188, 190, and 192 respectively (not shown) and directed to the IRE 174 through a beveled end 163 at a 90 degree angle thereto, striking the impacted aerosol and adsorbed vapor 178 at a 45 degree angle thereto. The infrared light 180 undergoes multiple reflections as it is internally reflected along attenuated light path 220, attenuating certain wavelengths of the infrared light 180. This geometry allows the evanescent wave of the infrared light 180 that penetrates the outer surface 176 to interact with the impacted aerosol and adsorbed vapor 178. These attenuated wavelengths are identified when the infrared light 180 is detected by the infrared light detector 184 and processed in spectrometer 204. The dedicated microcomputer 206, whether internal to the spectrometer 204 or electrically connected thereto by an electrical connection 222, (as shown in FIG. 1) uses commercially available software and, with a monitor and plotter (not shown), processes the data obtained and identifies the vapor sample 12.

The pair of opposing slit nozzles 170 are depicted in FIG. 9, where the opposing slit nozzles 170 are selected to provide sufficient velocity such that the fine particles 146 impact the IRE 174. The opposing slit nozzles 170 have nozzle inlets 224 formed in a nozzle housing 226, joined to, and in fluid communication with, a pair of supply conduit outlets 228 formed in the opposing supply conduits 138. Further included in the opposing slit nozzles 170 are a pair of nozzle outlets 230 formed by the nozzle housing 226 opposite the outer surfaces 176 of the IRE 174.

Referring now to FIG. 10, the coarse particle collector 164 is shown in greater detail. The fraction of the coarse particles 144 enter the coarse particle collector 164 at a collector inlet 232 formed by a collector housing 234 and which is connected to, and in fluid communication with, the coarse supply conduit 154 (not shown). The coarse particles 144 pass through the internal filter 166 which collects the coarse particles 144 in the second fraction to be either analyzed or discarded, while the air stream 109C exits through a collector exhaust 236 formed in the collector housing 234. If the coarse particles 144 are to be analyzed, the moveable mirrors 192 (not shown in FIG. 10) are rotated to the second position 200 so that the infrared light 180 travels along the second light path 202 and is analyzed in the spectrometer 204, similar to the fine particles 146 described above. A plurality of O-rings 238 are provided as needed to seal the coarse particle collector 164 from the outside environment. If needed, an ultra-fine particle collector (not shown) would be constructed in a manner similar to the coarse particle collector 164 described above.

Referring again to FIG. 1, the air stream 109 (and consequently 109*ex*) is created by the vacuum pump 208 with a pump inlet 240 and a pump exhaust 242 opposite the pump inlet 240. A first air conduit 244 having a first and second ends 246 and 248 respectively, is joined to, and in fluid communication with, a second flow meter 250, where the first end 246 is joined to the exhaust filter 140 and the second end 248 is joined to an inlet 252 in the second flow meter 250. The second flow meter 250 is fluidly connected to a second flow valve 254, which act in concert to control the air streams 109 and 109ex (where 109ex is comprised of the recombined air streams 109A, 109B, and 109C recombined at the outlet port 136) at a constant rate, nominally 60 LPM. The rate is measured by a flow meter control device 256 connected to the second meter 250 by an electrical connection 258.

This preferred flow rate controls the gas-particle reaction time, the relative size fractions in the virtual impactor 142 and the size of the particles that impact the IRE 174. In turn, the second flow valve 254 is connected to, and in fluid communication with, a second air conduit 260, where the second flow valve 254 has an outlet 262 connected to a first end 264 of the second air conduit 260 and the pump inlet 240 of the vacuum pump 208 is connected to a second end 266 of the second air conduit 260. Additionally, the pump exhaust 242 is joined to, and in fluid communication with, an exhaust conduit 268 at a first exhaust end 270 thereof, where the pump exhaust conduit 268 also has a second exhaust end 272 opposite the first exhaust end 270 in fluid communication with the surrounding environment or alternatively joined to, and in fluid communication with, the air inlet 18 (not shown) such that a portion of the air stream 109ex provides a source for the clean air 11. Preferably, the first air, second air, and exhaust conduits 244, 260, and 268 respectively are tubes each having an inlet and an outlet opposite the inlet.

In operating the vapor sample detection system 10 as depicted, the air flow 20 entrains the clean air 11 through the air flow delivery conduit 30 in the general direction indicated by arrow A at the preferred rate of 5 LPM. A supply of aerosol 38 is generated by the aerosol generator 36, which is in fluid communication with the air flow delivery conduit 30, so that a significant amount of the aerosol 38 becomes suspended in the air flow 20 forming the suspended aerosol 56. In turn, the suspended aerosol 56 is transported to the drying chamber 80 in the drying receptacle 70 by the aerosol delivery conduit 66, where water associated with the suspended aerosol 56 evaporates forming the dried suspended aerosol 84. Drying the suspended aerosol 56 reduces its effective median particle size enabling the dried suspended aerosol 84 to be transported through the vapor sample detection system 10 with minimal wall loss.

As hereinbefore set forth, the dried suspended aerosol 84 is transported to the mixing receptacle 94 via the dried aerosol delivery conduit 86, where the dried suspended aerosol 84 is mixed with the vapor 14 in the mixing chamber 108, forming the aerosol and adsorbed vapor 116. Preferably, the surrounding natural background particles 16 are filtered out of the vapor sample 12 as the vapor sample 12 is drawn up into the mixing chamber 108 by the air stream 111.

Finally, the vapor 14 is detected and analyzed. First, the aerosol and adsorbed vapor 116 are separated into a plurality of fractions having different sized particles using the virtual impactor 142. One of the plurality of fractions containing the coarse particles 144 is transported to the coarse particle collector 164 by the third air stream 109C for analysis and/or disposal. The fraction containing the vapor sample 12 and the fine particles 146 is transported by the first and second air streams 109A and 109B through the opposing supply conduits 138 to a pair of opposing slit nozzles 170, where the fine particles 146 are impacted on the at least one IRE 174. Any ultra-fine particles inadvertently collected would follow the first and second air streams 109A and 109B around the at least one IRE 174 and be discarded. In this manner, only the fine particles 146 impact and adhere to the outer surface 176 of the at least one IRE 174, forming the impacted aerosol and adsorbed vapor 178 on the outer surface 176.

The infrared light 180 is focused by the mirrors, parabolic mirrors, and moveable mirrors 188, 190, and 192 respectively and directed through the IRE 174 at a 45 degree angle thereto. The infrared light 180 strikes the impacted aerosol and adsorbed vapor 178 as it is internally reflected therethrough along attenuated light path 220, attenuating certain wavelengths of the infrared light 180. These attenuated wavelengths are identified when the infrared light 180 is detected by the infrared light detector 184 and processed in the spectrometer 204. The dedicated microcomputer 206, whether internal to the spectrometer 204 or electrically connected thereto by an electrical connection 222, then uses commercially available software and, with a monitor and plotter, processes the data obtained and identifies the vapor 14.

The present vapor sample detection system 10 satisfies the objectives set forth above. One objective is to provide an improved vapor sample detection system 10 with high detection sensitivity. The present vapor sample detection system 10, using the suspended aerosol 56 in combination with the ATR impactor 162 has at least a minimum sensitivity of approximately 1.5 parts per million (ppm) for a 60-second collection time, while concentrations as high as 1000 ppm have been detected. A further objective is to provide an improved vapor sample detection system 10 that detects and analyses vapor samples 12 in near real time, i.e. on the order of two minutes. In tests, the present vapor sample detection system 10 was able to detect high concentrations of vapor 14 in about 15 seconds, because only 10 spectral scans were required. Very low concentrations of the vapor 14 required more than 50 spectral scans, increasing the analysis time to approximately two and a half minutes. Finally, another objective is to provide an improved vapor sample detection system 10 that is mobile. Using the aerosol generator 36 in combination with the ATR impactor 162, means that the long single beam paths, multiple beam paths, high powered light sources, and/or the preconcentration methods of prior art vapor sample detection systems are no longer required. Thus, the present vapor sample detection systems 10 is not only faster and more sensitive, but is also mobile.

EXAMPLES

1. In tests, when an aerosol 38 is generated from dissolved chemicals in an aqueous solution, preferably cupric chloride, cupric sulfate, and magnesium oxide, a suspended aerosol 56 with a mass median aerodynamic diameter of about 0.65 micrometers was formed. This means that about 70% of the total surface area of the suspended aerosol 56 is associated with particles smaller than 0.65 micrometers and 99% of the area is associated with particles smaller than about 1.5 micrometers, which corresponds to the evanescent wave penetration depth of the infrared light 180 at the surface of the IRE 174.

2. Before operating the complete vapor sample detection system 10, it was necessary to verify the ability of the candidate aerosol materials 52 to adsorb trace quantities of dimethly methly phosphonate (DMMP) and allow it to be detected with the IAA infrared measurement technique. Copper (II) chloride ($CuCl_2$) has been found effective as a binding agent on gold surfaces to capture DMMP, while copper(II) sulfate ($CuSO4\ 5H_2O$) and magnesium oxide (MgO) were selected as alternate materials 52. $CuCl_2$ was the first of the candidate aerosol materials 52 to be tested. Background experiments were conducted by depositing a $CuCl_2$ aerosol onto the IRE 174. Since $CuCl_2$ does not have any absorption bands in the mid-infrared region and it does not interfere with bands attributable to trace gases, only bands of collected ambient atmospheric gases were present in the spectra. The IRE 174 containing the $CuCl_2$ deposit was placed in a receptacle containing a small open vial of liquid DMMP. After a 10 minute exposure to the DMMP vapors, the IRE was placed in the IAA and analyzed by the spectrometer. Characteristic infrared bands of DMMP were present after the 10 minute exposure. Because of safety considerations, the DMMP was not handled outside of a fume hood so no real-time, direct exposure experiments were conducted with the DMMP.

3. MgO was the second candidate aerosol material 52 to be tested for its DMMP vapor adsorbing characteristics. The results were not as promising as those obtained using the $CuCl_2$. The MgO and DMMP both have absorbance bands in the same infrared region, complicating identification of either species. Although MgO did adsorb DMMP vapors, the signatures were not nearly as strong as those obtained with $CuCl_2$ even after prolonged exposure. Furthermore, the low solubility of the MgO did not make a very suitable solution to produce the proper sized suspended aerosol 56. It was concluded that MgO was not a suitable candidate for further study.

4. Ammonia was selected as a trace gas to test the entire concept of the vapor sample detection system 10, since it is much easier to quantify and vary the gas concentration of ammonia as compared to DMMP. Known amounts of $NH_3$ were injected into the mixing chamber 108 via the injection ports 92 using either $CuCl_2$ or $CuSO_4$ aerosol material 52 as described earlier. It was observed that, in addition to the expected absorbance bands for the ammonium ion in the regions 2680–3500 $cm^{-1}$ and 1400 $cm^{-1}$, an unexpected peak occurred at 1272 $cm^{-1}$. This band was determined to be due to an ammonia complex formed with the copper ion of the aerosol material 52. The formation of the complex, represented by the 1272 $cm^{-1}$ absorbance band, is fortuitous since that particular peak is specific to the complex and the complex is not easily desorbed. It also leads to the possibility that a wide range or complexes between judiciously selected aerosol materials 52 and trace gases may be used to identify vapor samples 12.

5. Tests using a dry nitrogen carrier gas and a dried aerosol material 52 showed a marked decrease in the 1272 $cm^{-1}$ absorbance band when compared to similar experiments with either the dry nitrogen gas passed through a bubbler to humidify the gas or when a wet aerosol was used in the mixing chamber 108. This clearly indicates that moisture is an important component for the formation of the complex. Sufficient moisture was added by allowing the output of the aerosol generator 36 to pass directly into the mixing chamber 108 without passing through the drying receptacle 70.

Using this test arrangement, the quantity of ammonia captured on $CuSO_4$ aerosol was measured. This measurement compared the initial quantity of ammonia gas for six different injected volumes ranging from 0.2 ml to 20 ml, to the quantity of ammonia collected from the gas exhausted from the exhaust conduit 268 after the aerosol and adsorbed ammonia 116 had been impacted on the IRE 174. The exhaust gas was bubbled through distilled water to adsorb the ammonia left in the air stream 109. The solution was titrated to obtain a quantitative measure of the ammonia adsorbed in the solution. When compared to the initial quantity of ammonia injected, the measured quantities of ammonia collected in the titrated solution indicated that the mixing chamber 108 allows an average of 99.5%±0.6% of the injected $NH_3$ gas to be adsorbed by the suspended aerosol 56.

Figure 11:
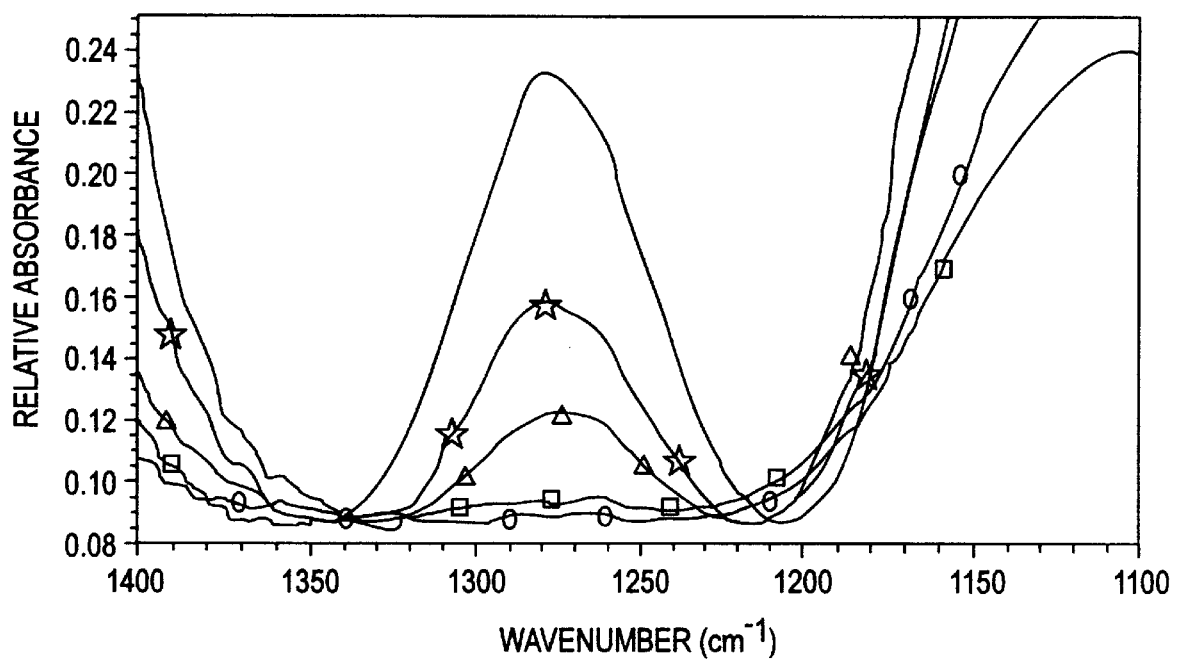
FIG. 11 is a graphical depiction of the 1272 $cm^{-1}$ absorbance band for the ammonia-copper complex collected on copper(II) sulfate aerosol.

6. The response of the vapor sample detection system 10 to the presence of ammonia vapor was determined by measuring the adsorbance at 1272 $cm^{-1}$, as a function of the volume of $NH_3$ gas injected into the mixing chamber 108. To illustrate the change in adsorbance with concentration, spectra for concentrations of 13, 167, 333, and 1000 ppm, representing injections of 0.8, 10, 20, and 60 ml of $NH_3$ respectively, are overlaid and presented in FIG. 11. Referring to FIG. 11 wavelength is plotted against adsorbance for $NH_3$, where the spectra for 0 ppm concentration is identified by the line with circles, the spectra for 13 ppm concentration is identified by the line with squares, the spectra for 167 ppm concentration is identified by the line with triangles, the spectra for 333 ppm concentration is identified by the line with stars, and the spectra for 1000 ppm concentration is identified by the solid line. The results of all of the test measurements are plotted in FIG. 12, as $NH_3$ in Air (ppm) is plotted against infrared adsorbance at 1272 $cm^{-1}$, where the gas concentration is calculated from the known gas quantity injected, the volumetric flow rate of the air through the system (60 LPM) and the sample collection time (60-seconds). The data for ammonia, collected with a wet aerosol, is plotted over three decades on a log-log plot to emphasize the range of concentrations that can be detected. It is generally expected that a linear relation exists between the quantity of gas molecules and the measured IR adsorbance. The nonlinearity of the data for ammonia seems to be due to the family of complexes formed with the $CuCL_4$. When the data is plotted on a linear scale, different concentration levels are best fit with different slopes. This implies a different complex, or a different balance of complexes, form at different levels.

Figure 12:
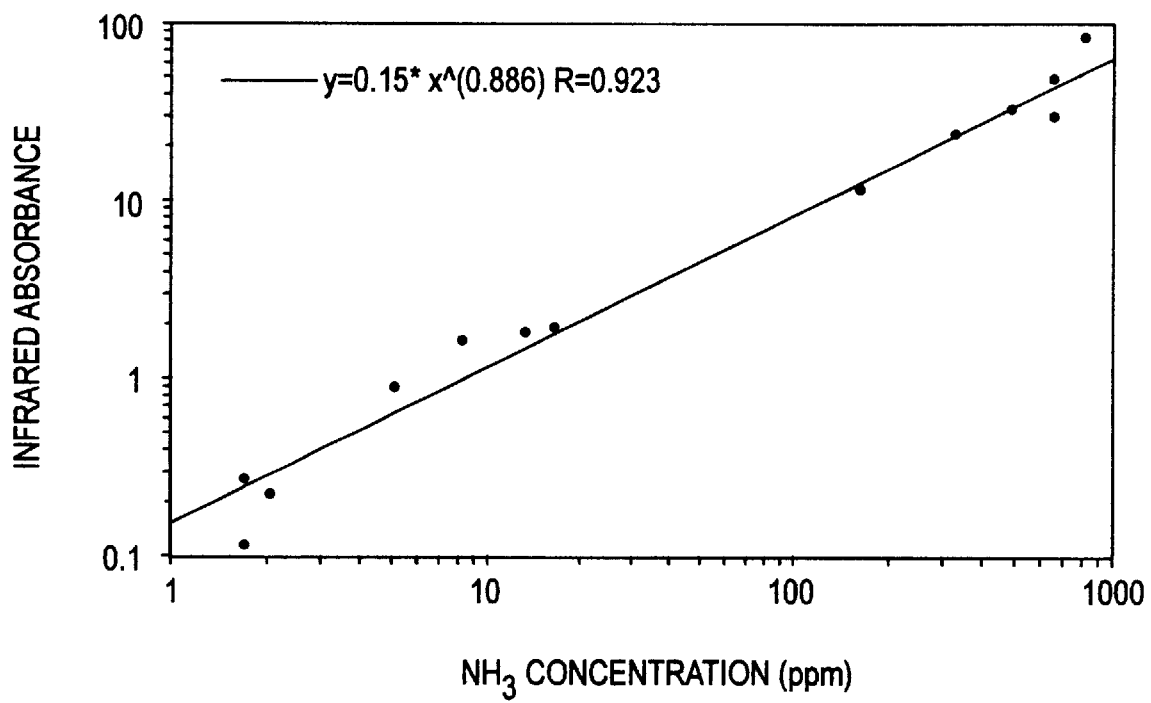
FIG. 12 is a graphical depiction of the measured infrared absorbance of the ammonia-copper complex at 1272 $cm^1$ as a function of ammonia gas concentration in air.

Further analysis of the data in FIG. 12 indicates that the minimum sensitivity for the 60-second collection time of the depicted detector system is approximately 1.5 ppm. Concentrations as high as 1000 ppm were detected with no evidence of saturating the surface of the suspended aerosol 56 with ammonia. However, an upper limit to the range of the instrument is expected, due to the limited surface area on the suspended aerosol 56. There is also the limitation that the aerosol cannot be collected indefinitely (i.e., allowed to pile up on the outer surface 176 of the IRE 174) without exceeding the interaction range of the evanescent wave.

7. There was some concern that the number of scans that could be coadded might be limited by desorption of the trace gas. To address this concern, the magnitude of the $NH_3$ infrared band at 1272 $cm^{-1}$, was followed as a function of time for one 50 ml injection test. Essentially no decrease in adsorbance was observed after 10 minutes. During the 10 minute test, the observed adsorbance varied by ±2.5% for the separate measurements. The observed variance is considered to be within the precision of the vapor sample detection system 10.

8. Tests to determine the ability of the apparatus to detect $SO_2$ gas using $CuCl_2$ aerosol material 52 were also successful, as evidenced by the appearance of the sulfate band at 1109 cm$^{-1}$ in the analyzed spectrum. There was no indication of the formation of a complex as was the case with ammonia gas. Since there was no evidence of a complex formed between the copper (II) and SO$_2$, separate experiments were conducted using pure water and sodium chloride (NaCl) as the gas adsorbing aerosol material 52, to determine whether the SO$_2$ collection was reliant upon the properties of the suspended aerosol 56.

Tests employing a pure water aerosol material 52 in place of the CuCl$_2$, resulted in only the gas phase SO$_2$, peaks at 1380 cm$^{-1}$ and 1350 cm$^{-1}$ being observed in the adsorbance spectrum and then, only at relatively high SO$_2$ concentrations. If the vacuum pump 208 was turned off, the observed gas phase SO$_2$ peaks remained relatively unchanged after 10 minutes. If the vacuum pump 208 continues to produce the air stream 109 without additional SO$_2$ gas injections, the spectral bands indicative of gaseous SO$_2$ disappeared after 10 minutes. These results demonstrate that only gas phase SO$_2$ was being detected when using a pure water aerosol material 52. Similar results were obtained with the NaCl aerosol material, demonstrating that the chemical properties of the aerosol materials are crucial to the function of the vapor sample detection system 10.

Figure 13:
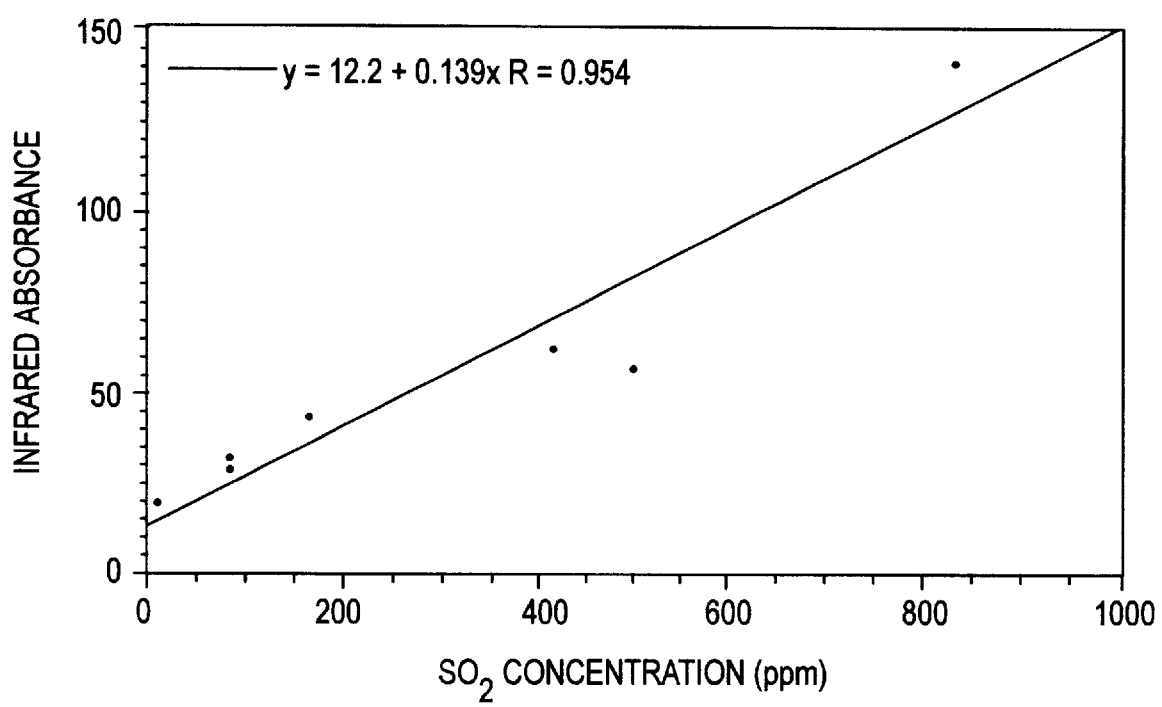
FIG. 13 is a graphical depiction of the measured infrared absorbance of sulfur dioxide at 1109 $cm^{-1}$ as a function of $SO_2$ concentration in air.

FIG. 13 shows the relationship between the amount of SO$_2$ injected and the measured adsorbance, where SO$_2$ in Air (ppm) is plotted against infrared adsorbance at 1109 cm$^{-1}$. The minimum concentration of SO$_2$ in air detected by the system for a 60-second collection time, based on a measured background of approximately 0.01 adsorbance units (a.u.) is 2.3 ppm. This level was obtained from a 0.14 ml injection of SO$_2$ into the system over the 60-second collection time with a 60 LPM air flow rate. The maximum concentration of SO$_2$ measured in these tests was 500 ppm. Measurements of higher concentrations are possible up to the limit of the suspended aerosol 56 surface area available for adsorption.

While a particular embodiment of the vapor sample detection system and method has been shown and described, it will be appreciated by those skilled in the art that changes and modifications may be made thereto without departing from the invention in its broader aspects as set forth in the following claims.

What is claimed is:

1. A mobile vapor sample detection method, the vapor sample including vapor and any ambient air and surrounding natural background particles, comprising the steps of:

generating a supply of aerosol having a particular effective median range;

mixing said aerosol with the vapor sample suspended in an air stream forming an aerosol and adsorbed vapor suspended in said air stream, thereby collecting the vapor sample from the ambient air and adsorbing the vapor sample onto the aerosol;

impacting said aerosol and adsorbed vapor upon at least one reflecting element and alternatively directing infrared light to said impacted aerosol and adsorbed vapor on said at least one reflecting element; and detecting and analyzing said alternatively directed infrared light using a spectrometer and a microcomputer and identifying the vapor sample.

2. The vapor sample detection method of claim 1 further including drying and reducing said aerosol by passing said aerosol into a drying chamber so that any water associated therewith evaporates prior to mixing said aerosol with the vapor sample.

3. The vapor sample detection method of claim 2 further including filtering out the surrounding natural background particles from the ambient air and from the vapor sample prior to forming said aerosol and adsorbed vapor.

4. The vapor sample detection method of claim 3 wherein said filtering is performed by a HEPA filter.

5. The vapor sample detection method of claim 3 wherein said mixing is performed in a mixing chamber.

6. The vapor sample detection method of claim 3 further including separating said aerosol and adsorbed vapor into a plurality of fractions having different sized particles.

7. The vapor sample detection method of claim 6 wherein said separating is performed by a virtual impactor.

8. The vapor sample detection method of claim 6 wherein one fraction of said plurality of fractions comprises particles having an aerodynamic diameter of about 0.3 micrometers to about 2.5 micrometers.

9. The vapor sample detection method of claim 6 wherein said impacting is performed by a pair of opposing slit nozzles directing said one fraction of said plurality of fractions against an outer surface of said at least one internal reflecting element.

10. The vapor sample detection method of claim 1 wherein said air stream is created by a vacuum pump.

11. A vapor sample detection system, the vapor sample including vapor and any ambient air and surrounding natural background particles, comprising:

a means for generating a supply of aerosol having a particular effective median particle size, said generating means having an inlet port and an outlet port so that a significant amount of said aerosol is provided at said outlet port;

a means for mixing said aerosol suspended in an air stream with the vapor, said mixing means having a vapor sample inlet port in fluid communication with said outlet port, an exhaust port, and a mixing chamber provided with an air stream, so that said aerosol adsorbs the vapor in said mixing chamber forming an aerosol and adsorbed vapor suspended in said air stream, thereby collecting the vapor sample from the ambient air and adsorbing the vapor sample onto the aerosol;

a means for detecting said aerosol and adsorbed vapor having an inlet port in fluid communication with said exhaust port, an exit port, at least one internal reflecting element that is impacted by said aerosol and adsorbed vapor suspended in said air stream, an infrared light emitter and an infrared light detector, so that infrared light can be alternatively directed to said impacted aerosol and adsorbed vapor on said at least one internal reflecting element; and a means for analyzing said infrared light having an spectrometer electrically connected to said infrared light emitter and said infrared light detector and a microcomputer, so that said infrared light is measured after being alternatively directed to said impacted aerosol and adsorbed vapor and the vapor sample identified.

12. The vapor sample detection system of claim 11 further including a means for drying and reducing said aerosol having an inlet aperture connected to said outlet port of said aerosol generating means and an outlet aperture connected to said inlet port of said mixing means so that any water associated with said aerosol evaporates.

13. The vapor sample detection system of claim 12 wherein said mixing means further includes a means for filtering said vapor sample connected so that the surrounding natural background particles in the vapor sample are separated from the vapor and the ambient air.

14. The vapor sample detection system of claim 13 further including a means for separating said aerosol and adsorbed vapor, so that said aerosol and adsorbed vapor are separated into a plurality of fractions having different size particles.

15. The vapor sample detection system of claim 14 wherein said separating means further includes a virtual impactor.

16. The vapor sample detection system of claim 14 wherein one fraction of said plurality of fractions comprises particles having an aerodynamic diameter of about 0.3 micrometers to about 2.5 micrometers.

17. The vapor sample detection system of claim 14 wherein said detection means further includes a pair of opposing slit nozzles which direct said one fraction of said plurality of fractions against an outer surface of said at least one internal reflecting element.

18. The vapor sample detection system of claim 13 wherein the vapor sample detection system is mobile.

19. The vapor sample detection system of claim 18 wherein said air stream is generated by a vacuum pump.

20. A mobile vapor sample detection system, the vapor sample including vapor and any ambient air and surrounding natural background particles, comprising:

a vacuum pump for generating a stream of air;

an aerosol generator having an inlet port and an outlet port for generating a supply of aerosol having a particular effective median particle size so that a significant amount are provided at said outlet port;

a dryer having an inlet aperture connected to said outlet port of said aerosol generator and an outlet aperture so that any water associated with said aerosol evaporates;

a mixer having a vapor sample inlet port connected to said outlet aperture of said dryer, a filter connected to said vapor sample inlet port for separating the surrounding natural background particles from the vapor and the ambient air, an exhaust port, and a mixing chamber provided with an air stream for mixing said aerosol with the vapor, so that said aerosol adsorbs the vapor forming aerosol and adsorbed vapor suspended in said air stream, thereby collecting the vapor sample from the ambient air and adsorbing the vapor sample onto the aerosol;

a detector having an inlet port in fluid communication with said exhaust port, an exit port, a virtual impactor for separating said aerosol and adsorbed vapor into a plurality of fractions having different size particles, a pair of opposing slit nozzles which direct and impact a first fraction of said plurality of fractions against an outer surface of an at least one reflecting element, and an infrared light emitter and an infrared light detector, so that said infrared light can be alternatively directed to said impacted aerosol and adsorbed vapor on said internal reflecting element; and an analyzer having a spectrometer electrically connected to said infrared light emitter, said infrared light detector and a microcomputer so that said infrared light can be measured after being alternatively directed to said impacted aerosol and adsorbed vapor on said internal reflecting element and the vapor sample identified.

* * * * *